United States Patent [19]

Borglum

[11] 4,347,320
[45] Aug. 31, 1982

[54] IMMOBILIZATION OF MICROORGANISMS IN GELLED CARRAGEENAN

[75] Inventor: Gerald B. Borglum, Elkhart, Ind.

[73] Assignee: Miles Laboratories, Inc., Elkhart, Ind.

[21] Appl. No.: 209,411

[22] Filed: Nov. 24, 1980

[51] Int. Cl.$^3$ .......................... C12P 7/48; C12P 7/06; C12N 11/10

[52] U.S. Cl. .................................. 435/144; 435/161; 435/178; 435/182

[58] Field of Search ............... 435/144, 161, 174, 177, 435/178, 180, 182

[56] References Cited

U.S. PATENT DOCUMENTS 3,402,103 9/1968 Amberg et al. ................. 435/161 X
3,940,315 2/1976 Hustede et al. ...................... 435/144
4,138,292 2/1979 Chibata ................................ 435/178
4,288,552 9/1981 Gestrelius ....................... 435/177 X Primary Examiner—David M. Naff
Attorney, Agent, or Firm—J. D. McNeil

[57] ABSTRACT

Microorganisms are immobilized by mixing the microorganisms with an aqueous solution of kappacarrageenan and gelling the resultant mixture by the addition of an epihalohydrin: alkylene polyamine polymer having a mole ratio of from about 0.60:1 to 2.7:1 and a molecular weight of from 4,000 to 50,000 or by the addition of polyethyleneimine having a molecular weight of 300 to 50,000. Preferred microorganisms are *Aspergillus niger* and *Saccharomyces cerevisiae* which are respectively used to produce citric acid and ethanol.

6 Claims, No Drawings

IMMOBILIZATION OF MICROORGANISMS IN GELLED CARRAGEENAN

BACKGROUND OF THE INVENTION

1. Field of the Invention

It is known that viable microorganisms, which are proteinaceous in nature, have extensive commercial uses. Microorganisms, including bacteria, yeast and fungi are capable of use in widely divergent fields. U.S. Pat. No. 3,438,863 discloses the use of *Aspergillus niger, A. clavatus, A. wentii, Pencillium citrinum* and *P. luteum* for citric acid production. U.S. Pat. No. 3,265,586 discloes bacterial alpha amylase enzymes derived from strains of *Bacillus subtilis*. Lactic-acid producing bacteria such as *Streptococcus lactis, S. cremoris* and *S. diacetilactis* are disclosed in U.S. Pat. No. 3,483,087. The production of galactose oxidase is disclosed in U.S. Pat. No. 3,186,921. The commercial production of ethanol from various yeast strains, e.g. Saccharomyces, is well known in the art. Because of an interest in decreasing consumption of petroleum products, the use of ethanol in internal combustion engines is receiving increased attention.

In many uses of viable microorganisms, the reaction is conducted in a reactor using a "batch" process. A large capital investment is required for the batch reactor equipment, in addition to the large space requirements and the amounts of energy required.

At present, citric acid, for example, is produced in large batch reactors which have a capacity of as much as 30,000 gallons. A fermentation substrate is prepared with suitable nutrients in a reactor, inoculated with citric acid-producing strains of *A. niger* and allowed to ferment. During fermentation, the reactor contents are continuously stirred. After fermentation, the contents of the reactor are removed, the mycelium filtered and citric acid recovered.

In the traditional "batch" method to make ethanol, a fermentable substrate is put into a reactor and inoculated with yeast. Here agin, during fermentation the contents are agitated. After fermentation, the reactor contents are removed, the mycelium separated and the alcohol solution recovered.

It is a goal in numerous applications involving viable microorganism to develop processes involving a fixed bed, where the microorganism is immobilized, a substrate is passed through the bed, and the product produced by the microorganism recovered. A successful fixed bed system would reduce the costs referred to above and reduce effluent problems by allowing reuse of the microorganisms.

Thus, it is a goal of research in citric acid production to develop processes involving a fixed bed, where the *A. niger* or other suitable cells are immobilized, a fermentation substrate is passed through the bed, and citric acid recovered. It is also a goal in ethanol production to develop processes involving a fixed bed, where the yeast cells are immobilized, the feedstock flows in continuously at one end of the bed, and the alcohol-containing mixture flows out the other end of the bed.

One method of immobilizing such microorganisms is by encapsulating the microorganisms within the gel lattice of a polymer. While this method of immobilizing microorganisms has an advantage in that the reaction conditions utilized to accomplish the entrapment are sufficiently mild so that often there is little alteration or deactivation of the microorganisms, it also had disadvantages in that the gel produced has poor mechanical strength. Low mechanical strength can produce compacting of the gel containing the microorganisms, which can cause plugging of the reaction system.

2. Prior Art

In *Enzyme Microb. Technol.*, Vol. 1, 95–99 (1979), immobilization techniques using kappa-carrageenan for immobilization of *Escherichia coli* are described. Gel-inducing agents, such as various metal ions, amines and ammonium ions, are suggested. Also described is stabilization of the activity of the microorganisms by treating the immobilized cells with glutaraldehyde; also described is hardening the gelled material with a mixture of glutaraldehyde and hexamethylenediamine and a salt such as KCl. In *J. Solid-Phase. Biochem.*, Vol. 2, 225–236, (1978) various methods for immobilizing glucose isomerase-producing microbial cells in kappa-carrageenan with gel-inducing ions, e.g. $K^+$, $NH_4^+$, and $Ca^{2+}$, are described. The immobilized cells were treated with glutaraldehyde; glutaraldehyde and gelatin; and glutaraldehyde and hexamethylenediamine to improve the characteristics of the gel. The authors indicate that when the k-carrageenan immobilized cells were treated with hexamethylenediamine and glutaraldehyde, glucose isomerase activity was increased.

U.S. Pat. No. 4,138,292 is directed to immobilizing catalytically active substances and microorganisms. The patentee enumerates approximately two dozen catalytically-active microorganisms which can be immobilized. The patentee's procedure involves treating k-carrageenan with ammonium ion, a metal ion, a water-soluble organic amine or a water-miscible organic solvent. Approximately 50 organic amines are listed as being suitable for use as a gelling agent.

In column 7, the patentee suggests that the immobilized catalytically active substance may be further treated with a gel-hardening agent; approximately two dozen compounds are listed as being operable, including ammonia or an alkylenediamine and followed by reaction with an aliphatic dialdehyde, e.g., glutaraldehyde.

SUMMARY OF THE INVENTION

The present invention is directed to a method of immobilizing viable microorganisms in k-carrageenan by mixing the microorganisms and k-carrageenan together and gelling the mixture with an epihalohydrin alkylene polyamine polymer or with polyethyleneimine. The invention is also directed to methods of producing citric acid and ethanol from immobilized microorganisms.

DETAILED DESCRIPTION OF THE INVENTION

The k-carrageenan used in the present invention is a polysaccharide composed of unit structures of $\beta$-D-galactose sulfate and 3,6-anhydro-$\alpha$-D-galactose. The molecular weight ranges from 100,000 to 800,000 with an ester content of from about 20 to 30 percent of the unit weight. K-carrageenan is commercially available from Sigma Chemical Co., St. Louis, Mo.

The *A. niger* cells were obtained from five day old *A. niger* citric acid fermentation. *A. niger* microbial cultures are available from numerous sources, including American Type Culture Collection (ATCC), Rockville, Md. The yeast cells were obtained from commercially available yeast cultures.

The k-carrageenan and microorganisms are mixed together at a temperature of about 25° to 50° C., preferably about 40° C. The mixture can be made into beads by forming droplets through a nozzle, or can be made into membranes by spreading on a plate or sheet or can be made into fibers. After formation of the microorganism k-carrageenan mixture, the mixture is gelled by contact with an aqueous solution containing from about 4 to 16 percent (w/v) of a gelling agent.

The presence of calcium ions in the k-carrageenan can produce an increase in viscosity which could make processing more difficult. Accordingly, it may be desirable to add disodium ethylenediaminetetraacetic acid (EDTA) to chelate the calcium ions. Alternatively, the fluidity can be increased by temperature control, i.e., by increasing the temperature to 50° C., the viscosity is decreased. Because the process involves viable microorganisms, the temperature range is restricted to the range in which the microorganisms will maintain their viability.

An operable pH for the mixture is within the pH range of about 5 to 10. At a pH lower than 5, EDTA is a poor chelating agent, and at a pH of higher than 10, maintaining maximum viability of the microorganisms may be difficult.

It is important that gelling of the k-carrageenan take place as rapidly as possible to avoid diluting the k-carrageenan to an extent that formation of gel beads, membrane, fibers, etc., will not occur. Accordingly, the gelling agent should be present in an amount of about 4 to 16 percent to produce efficient, rapid gelling.

The gelling agent should be maintained in contact with the gelled material for a time sufficiently long to allow the gelled material to harden throughout. The hardening period will be dependent upon the distance to the center of the gelled material.

The ratio of the amount of viable microorganisms to the amount of k-carrageenan does not appear to be critical in the immobilization process, especially since the microorganisms will continue to grow after immobilization.

The epihalohydrin-alkylene polyamine polymeric gelling agent used in the present invention is a water-soluble cationic polymeric material obtained by the polymerization of an epihalohydrin with an alkylene polyamine having the formula

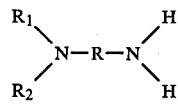

where R is a lower alkylene having from 2 to about 6 carbon atoms, e.g., ethylene, propylene, isopropylene, isopentyl, hexylene; $R_1$ and $R_2$ each are a lower alkyl of from about 1 to about 6 carbon atoms, e.g., methyl, ethyl, propyl, isopropyl, pentyl, hexyl, isohexyl, etc. The mole ratios of the epihalohydrin to the alkylene polyamine are from about 0.60:1 to about 2.7:1. The molecular weight of the polymer is from about 4,000 to 50,000. The polymerization reaction is conducted by reacting with the alkylene polymer from about 50 to 90 percent of the amount of epihalohydrin to be polymerized, allowing the reactor to continue until the reaction medium attains a substantially uniform viscosity and reacting the remaining portion of the epihalohydrin incrementally to obtain the cationic polymer. A suitable epihalohydrin alkylene polyamine polymer is commercially available from Betz Laboratories, Trevose, Pa. under the designation Betz 1180 and is described in U.S. Pat. Nos. 3,953,330 and 3,915,904.

The polyethyleneimine gelling agent used in the present invention has a molecular weight of about 300 to 50,000. Suitable polyethyleneimines in this molecular weight range are commercially available from American Hospital Supply Corporation, Scientific Products Division, Evanston, Ill. and Cordova Chemical Company, Sacramento, Calif., respectively.

Both the polyethyleneimine and the epihalohydrinalkylene polyamine polymer are effective in immobilizing microorganisms. Lower molecular weight compounds, e.g., 1200 molecular weight, are preferred because of easier diffusion into the gel.

EXAMPLE 1

K-carrageenan was dissolved to 2 percent w/v in a solution which contained 1 percent w/v NaCl (approximately isotonic)—1 percent EDTA. The EDTA at a pH of about 5, was present to chelate any calcium ions present and to improve fluidity. The temperature was maintained at about 50° C. A four ml portion of this solution, cooled to 40° C., was mixed with microbial cells filtered from a 10 ml portion of 5-day old *A. niger* citric acid fermentation. The mixture was transferred to a length of plastic tubing (used as a reservoir) held in a 40° C. bath to maintain fluidity. The mixture of *A. niger* and k-carrageenan was injected (displaced from the tubing by pumping water into the tubing) into a flowing stream of 40° C. mineral oil (in plastic tubing) to form droplets. The droplets were hardened by cooling in an ice bath to form beads. The beads were transferred into a test tube containing a gelling agent which was held in an ice bath. Samples of k-carrageenan beads containing immobilized *A. niger* microbial cells were prepared and gelled with about 50,000 molecular weight polyethyleneimine; duplicate samples were prepared and gelled with about 50,000 molecular weight epihalohydrinalkylene polyamine polymer.

The gelled k-carrageenan beads were washed with 0.9 percent w/v NaCl and transferred to 250 ml sterile Erlenmyer flasks. A 20 ml portion of a 14 percent w/v glucose solution containing nutrient salts, such as 0.015 weight percent $KH_2PO_4$, 0.1 weight percent $MgSO_4.7H_2O$, 50 ppm (by weight) $Ca^{2+}$ ions as $CaCl_2.2H_2O$ and 0.2 weight percent $(NH_4)_2CO_3$ was added to each flask, the flasks capped with sterile porous polyurethane plugs and placed on a rotary incubator shaker, at 120 rpm at a temperature of about 34° C. Suitable nutrient salt compositions are disclosed in U.S. Pat. No. 3,290,227 and 3,349,005.

The liquid was assayed daily for citric acid production by a pyridine-acetic anhydride method described in *Anal. Chem.* 34, 426–428 (1962). At 2 to 3 day intervals the beads were separated from the substrate, washed with water and transferred to fresh substrate. Each sample of *A. niger* immobilized in k-carrageenan beads produced a total of 5.2 to 5.3 g citric acid in 31 days.

As described in Example 2, further tests were conducted to compare the solubility of k-carrageenan beads using various gelling agents.

EXAMPLE 2

*A. niger* microbial cells were immobilized in 2 percent w/v or 3 percent w/v k-carrageenan, as described in Example 1 using the various gelling agents indicated below. Ten gel beads (1–2 mm diameter total volume of 0.012–0.042 ml) were transferred to 250 ml Erlenmeyer flasks and 100 ml distilled water or 100 ml 5 percent w/v citric acid, pH 1.5 was added. The flasks were placed on an incubator shaker, 160 rpm at 32°–34° C. Test results obtained are summarized below.

TABLE 1

| Sample Number | Gelling Agent | Days Used Water | Days Used Citric Acid |
|---|---|---|---|
| 1 | KCl | 1 (dissolved) | 1 (dissolved) |
| 2 | NH$_4$Cl | 1 (dissolved) | 1 (dissolved) |
| 3 | CaCl$_2$ | 1 (dissolved) | 1 (dissolved) |
| 4 | ethylenediamine | >3 | 1 (dissolved) |
| 5 | 1,6-hexanediamine | >3 | 1 (dissolved) |
| 6 | epihalohydrin-alkylene polyamine polymer; molecular weight of about 50,000 | >3 | >3 |
| 7 | polyethyleneimine; a series having a molecular weight of 300, 600, 1200, 1800 and a mixture of 20,000–30,000 | >3 | >3 |

Because the immobilized *A. niger* microorganisms are intended to produce citric acid, it is important that the immobilized cells be resistant to dissolving in water and citric acid. Beads prepared by gelling with the epihalohydrin-alkylene polyamine polymer and polyethylenediamine of the present invention were resistant to both water and citric acid. The diamine compounds and ionic gelling agents suggested in the prior art were not suitable for citric acid production from immobilized microorganisms.

As indicated earlier, the prior art has suggested the desirability of increasing the strength of gels containing immobilized microorganisms by subsequent treatment with glutaraldehyde or a glutaraldehydehexamethylenediamine mixture to harden the immobilized microbial cells. The prior art also indicated that an increase in strength was accompanied by an increase of activity of the immobilized microorganisms. As described below, comparative tests were conducted with immobilized *A. niger*, using various hardening agents, to determine the effect of hardening agents on the activity of the immobilized microorganisms in the production of citric acid.

EXAMPLE 3

The procedure described in Example 1 was used to immobilize *A. niger* in k-carrageenan. Gelling agents used were the epihalohydrin-alkylene polyamine polymer of Example 1 and 1,6-hexanediamine. Two preparations were made with each gelling agent; one preparation with each gelling agent was further treated with a hardening agent, glutaraldehyde, at a pH of 7 for 30 minutes. The four preparations were washed with 0.9 percent w/v NaCl and transferred to 45 ml sterile plastic centrifuge tubes. A 10 ml portion of the substrate of Example 1 was added, the tubes capped with sterile porous polyurethane plugs and placed on a rotary incubator shaker, at 250 rpm and 34° C.

The beads were then tested for stability and citric acid production. The results obtained are summarized in Table 2 below.

TABLE 2

| Sample Number | Gelling and/or Hardening Agent | Days Used | Total Citric Acid |
|---|---|---|---|
| 8 | 1,6 hexanediamine (3.1% w/v) | 4 (beads dissolved) | 0.22 |
| 9 | 1,6 hexanediamine and glutaraldehyde | 7 | 0.14 |
| 10 | epihalohydrin-alkylene polyamine and glutaraldehyde | 9 | 0.13 |
| 11 | no hardening treatment; gelled with epihalohydrin-alkylene polyamine | 18 | 1.0 |
| 12 | Control* | 4 | 0.45 |

*Unimmobilized *A. niger* transferred after 2 days fermentation to fresh substrate for additional two days fermentation The above test results indicate that hexamethylenediamine was not usable as a gelling agent without cross-linking with glutaraldehyde to prevent the beads from dissolving. However, cross-linking of the beads with glutaraldehyde to increase the strength of the gel greatly reduced the citric acid production (by greater than 40 percent).

The epihalohydrin-alkylene polyamine polymer gelled beads produced 1.0 gram of citric acid in 18 days. Hardening of these beads by cross-linking with glutaraldehyde, as taught in the prior art, did not appear to offer an advantage.

Therefore, the above test results indicate that the prior art suggestion of the desirability of increasing the gel strength by hardening with glutaraldehyde, and maximizing the microorganism activity was not applicable to immobilized *A. niger* microorganisms.

As described below, the method of the present invention was used to immobilize yeast and the immobilized yeast contacted with a fermentable substrate, for the production of ethanol.

EXAMPLE 4

K-carrageenan was dissolved to 2 percent w/v in water. The mixture was maintained at a temperature of about 40° C. Commercially available active dry yeast *Saccharomyces cerevisiae*, sold under the trade designation Red Star, Universal Foods Corp., Milwaukee, Wis., was slurried with water (0.3 g yeast/2 ml water), and held at 37° C. for 5 minutes for rehydration.

The yeast cells were immobilized in 8 ml of the 2 percent k-carrageenan prepared as described above, by the procedure described in Example 1. The immobilized yeast cells were gelled with about 50,000 molecular weight epihalohydrin-alkylene polyamine polymer. The gelled k-carrageenan beads were washed with water and transferred to 250 ml Erlenmyer flasks. A 100 ml portion of a 16 percent w/v glucose solution at a pH of 4, containing 1.05 percent nutrient broth was added to each flask. The nutrient broth added is a commercially available broth, sold under the trade designation Difco YM Broth, by Difco Laboratories, Inc., Detroit, Mich.

The flasks were stoppered and a tube led from the stopper to below the surface of water in another flask, used as an air trap. The flasks containing the immobilized yeast were placed on a rotary incubator shaker, at 160 rpm and 30° C. These immobilized bead samples were given the designation "A". A second series, given the designation "B" was prepared as above except 17 ml of 2 percent w/w k-carrageenan was used.

The fermentation flasks were sampled and assayed for ethanol by gas liquid chromatography.

TABLE 3

Ethanol Produced by Immobilized yeast

| Preparation | Days | w/w Ethanol |
|---|---|---|
| A | 1 | 0.14% |
| B |   | 0.75% |
| A | 2 | 0.14% |
| B |   | 0.79% |
| A | 3 | 0.16% |
| B |   | 0.91% |
| A | 6 | 0.21% |
| B |   | 1.38% |

As summarized in Table 3 above, the yeast microorganisms immobilized according to the present invention produced ethanol.

What is claimed is:

1. A method of preparing immobilized viable *Aspergillus niger* or *Saccharomyces cerevisiae* microorganisms which comprises the steps of mixing said microorganisms with an aqueous solution of kappa-carrageenan at a temperature of about 25° to 50° C. and gelling the mixture by the addition of a compound selected from the group consisting of an epihalohydrin:alkylene polyamine polymer having a mole ratio of from about 0.60:1 to 2.7:1 and a molecular weight of from 4,000 to 50,000 and polyethyleneimine having a molecular weight of from 300 to 50,000 to form a gel matrix containing said immobilized viable microorganisms.

2. A method of preparing immobilized catalytically active *Aspergillus niger* microorganisms which comprises the steps of mixing *Aspergillus niger* microorganisms with an aqueous solution of kappa-carrageenan at a temperature of about 40° C. and gelling the mixture by the addition of polyethyleneimine having a molecular weight of about 1200.

3. A method of producing citric acid which comprises the steps of contacting a carbohydrate-containing substrate with immobilized *Aspergillus niger* microorganism cells and recovering citric acid therefrom, said immobilized cells having been produced by mixing *Aspergillus niger* microorganisms with an aqueous solution of kappa-carrageenan at a temperature of about 25° to 50° C., and gelling the resulting mixture by the addition of a compound selected from the group consisting of an epihalohydrin:alkylene polyamine polymer having a mole ratio of from about 0.60:1 to 2.7:1 and a molecular weight of from 4,000 to 50,000 and polyethyleneimine having a molecular weight of from 300 to 50,000.

4. A method of producing citric acid which comprises the steps of contacting a carbohydrate-containing substrate with immobilized *Aspergillus niger* microorganism cells and recovering citric acid therefrom, said immobilized cells having been produced by mixing *Aspergillus niger* microorganisms with an aqueous solution of kappa-carrageenan at a temperature of about 25° to 50° C., and gelling the mixture by the addition of a polyethyleneimine having a molecular weight of about 1200.

5. A method of producing ethanol which comprises the steps of contacting a fermentable substrate with immobilized *Saccharomyces cerevisiae* microorganism cells and recovering ethanol therefrom, said immobilized cells having been produced by mixing *Saccharomyces cerevisiae* microorganisms with an aqueous solution of kappa-carrageenan at a temperature of about 25° to 50° C., and gelling the mixture by the addition of a compound selected from the group consisting of an epihalohydrin:alkylene polyamine polymer having a mole ratio of from about 0.60:1 to 2.7:1 and a molecular weight of from 4,000 to 50,000 and polyethyleneimine having a molecular weight of from 300 to 50,000.

6. A method of producing ethanol which comprises the steps of contacting a fermentable substrate with immobilized *Saccharomyces cerevisiae* microorganism cells and recovering ethanol therefrom, said immobilized cells having been produced by mixing *Saccharomyces cerevisiae* microorganisms with an aqueous solution of kappa-carrageenan at a temperature of about 25° to 50° C., and gelling the mixture by the addition of a polyethyleneimine having a molecular weight of about 1200.

* * * * *